Sept. 11, 1956 W. FLEMER III Plant Pat. 1,514
HONEYLOCUST TREE
Filed Nov. 16, 1955
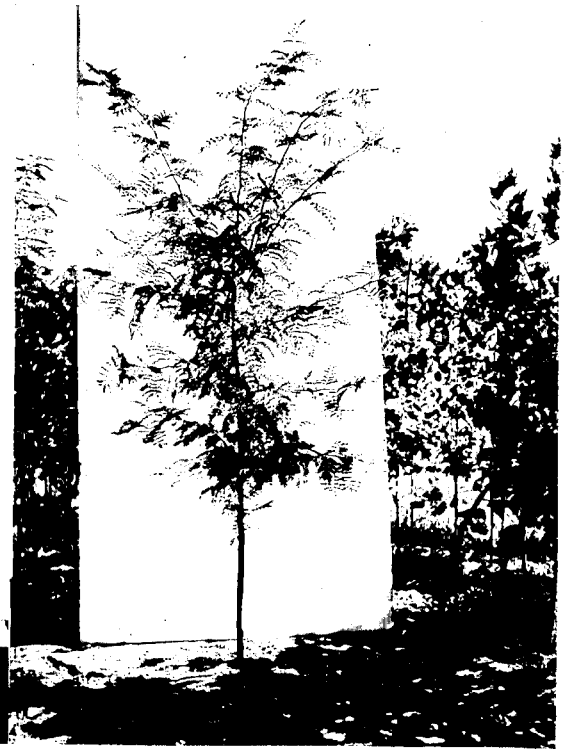
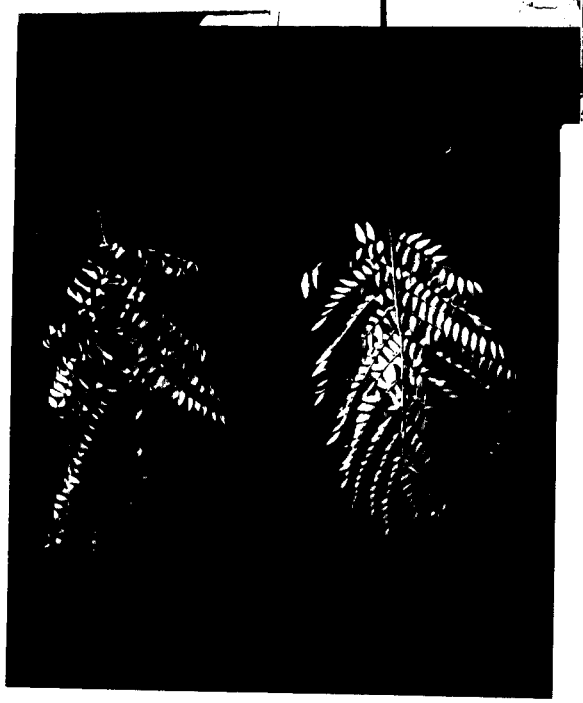
Inventor.
William Flemer, III
By: Robb & Robb
Attorneys.

United States Patent Office

Plant Pat. 1,514
Patented Sept. 11, 1956

1,514

HONEY LOCUST TREE

William Flemer III, Princeton, N. J., assignor to Wm. Flemer's Sons, Inc., trading as Princeton Nurseries, Princeton, N. J., a corporation of New Jersey Application November 16, 1955, Serial No. 547,346

1 Claim. (Cl. 47—59)

The present invention relates to a new and distinct variety of thornless honey locust tree which was discovered by me as a newly found seedling of *Gleditsia triacanthus inermis* in transplanted blocks of seedlings of the latter variety which were being grown under my control, direction and supervision in Plainsboro township, Plainsboro, New Jersey. At the time of my discovery, the new seedling was about 10 feet tall, and my attention was initially drawn thereto by its very close, finely divided and dense foliage, its straight trunk, straight branches, and its spreading and symmetrical top or head, all of which features were unique and distinct as compared with the common varieties then being grown by me and from all others of which I was aware.

Following my initial discovery, I promptly took steps to preserve and observe the new seedling, as well as to asexually reproduce the same by budding, as performed by me at Princeton, New Jersey. Continued observations of the original seedling and the asexual reproductions thereof have fully demonstrated that the aforementioned characteristics and distinctions are firmly established and are transmissible by asexual reproduction.

Although the parentage of my new seedling is not definitely known to me, I am convinced that it represents a new and improved variety which is distinct from all other varieties, as evidenced by its unique combination of characteristics which may be briefly summarized as follows, and which make my new variety an ideal type for lawn and yard planting around small homes, particularly because of its compact, slower growth, and its spreading habit:

(1) Straight trunk and branches, and the complete absence of drooping branches or wind-blown appearance;

(2) Symmetrical, spreading and full top or head, and the complete absence of any inclination to droop;

(3) Slow growth;

(4) Finely divided, close and dense foliage; and (5) The rich dark green color of the foliage:

The accompanying drawing shows a typical tree of my new variety, as well as typical specimens of the foliage thereof as the latter appears from both its upper and lower surfaces on an enlarged scale, all as depicted in color as nearly true as it is reasonably possible to make the same in a color illustration of this character.

The following is a detailed description of my new variety, with color terminology in accordance with Munsell's Color Chart, except where general color terms of ordinary dictionary significance are obvious:

Parentage: Newly found seedling of unknown parentage.

Propagation: Holds its distinguishing characteristics through succeeding propagations by budding (sometimes termed "bud-grafting").

Locality where grown and observed: Princeton, New Jersey.

Tree: Medium stature; vigorous; spreading; very dense; hardy; symmetrical; with ovate head; spreading and full top; with absence of any inclination toward drooping or crooked head.

*Growth.*—Slow; spreading.

*Trunk.*—Stocky; very straight; smooth.

*Branches.*—Stocky; very straight; smooth. Color—Dull Brown, Plate 5.0 YR 3/2.

*Lenticels.*—Numerous; small.

*Leaves.*—Large; bipinnate; from 20 to 22 pinnae per leaf and from 24 to 28 leaflets per pinna; finely divided; close; dense. Average length of leaves—From 25 to 30 cm. Average width of leaves—From 21 to 24 cm. Color: upper surface—Dark Nile Green, Plate 7.5 GY 3/4; Lower surface—Dark Nile Green, Plate 7.5 GY 4/6.

*Leaflets.*—Lanceolate. Average length of individual leaflets—from 1½ to 2 cm. Average width of individual leaflets—from 5 to 7 mm.

*Rachis.*—Sparingly pubescent; grooved.

*Margin.*—Remotely crenate-serrulate.

*Petiole.*—Medium length; thick.

*Glands.*—None.

*Stipules.*—Produced only on earliest leaves in growing season; from 1¾ to 2 cm. long.

Flower buds: Depressed; inconspicuous; small; globose; sparingly pubescent.

Flowers: Small; moderately abundant; only staminate flowers observed; blooms about mid-season as compared with other varieties. Color—Pale Lemon Yellow, Plate 7.5 Y 8/4.

Fruit: None observed.

Disease and insect resistance: Foliage has good resistance to spider mite damage and sun scorch as compared with other varieties grown under comparable cultural conditions at Princeton, New Jersey.

I claim:

A new and distinct variety of thornless honey locust tree, substantially as herein shown and described, characterized particularly as to novelty by its straight trunk and branches, its complete absence of thorns, its compact, symmetrical and spreading general form, its spreading, full and symmetrical top, its relatively slow growth, its complete absence of any wind-blown appearance in its top, and its finely divided, close, dense and rich dark green foliage.

No references cited.